United States Patent
Shinjo et al.

(10) Patent No.: US 10,519,367 B2
(45) Date of Patent: Dec. 31, 2019

(54) METAL ORGANIC FRAMEWORK, PHOSPHOR FILM, AND MOLECULE DETECTING DEVICE

(71) Applicant: Kabushiki Kaisha Toshiba, Minato-ku (JP)

(72) Inventors: Yasushi Shinjo, Kawasaki (JP); Hirohisa Miyamoto, Kamakura (JP); Satoshi Takayama, Kawasaki (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 0 days.

(21) Appl. No.: 16/118,553

(22) Filed: Aug. 31, 2018

(65) Prior Publication Data
US 2019/0292449 A1    Sep. 26, 2019

(30) Foreign Application Priority Data
Mar. 20, 2018   (JP) ................................ 2018-053473

(51) Int. Cl.
| | | |
|---|---|---|
| *B01D 53/02* | (2006.01) | |
| *B01J 20/22* | (2006.01) | |
| *C09K 11/06* | (2006.01) | |
| *C09K 11/02* | (2006.01) | |
| *B01J 20/34* | (2006.01) | |
| *G01N 21/64* | (2006.01) | |

(52) U.S. Cl.
CPC ............... *C09K 11/06* (2013.01); *B01J 20/22* (2013.01); *B01J 20/226* (2013.01); *B01J 20/3425* (2013.01); *B01J 20/3483* (2013.01); *C09K 11/025* (2013.01); *G01N 21/6428* (2013.01); *C09K 2211/1029* (2013.01)

(58) Field of Classification Search
CPC .................. C09K 11/06; C09K 11/025; C09K 2211/1029; B01J 20/22; B01J 20/226; B01J 20/3425; B01J 20/3483; G01N 21/6428
USPC ....................................................... 250/458.1
See application file for complete search history.

(56) References Cited

U.S. PATENT DOCUMENTS

| 6,783,873 B2 | 8/2004 | Tsuboyama et al. | |
|---|---|---|---|
| 7,687,432 B2 * | 3/2010 | Zhou ...................... | B01J 20/226 502/401 |
| 7,799,120 B2 * | 9/2010 | Yaghi ..................... | B01D 53/02 206/0.7 |

(Continued)

FOREIGN PATENT DOCUMENTS

| JP | 2003-73388 | 3/2003 |
|---|---|---|
| JP | 2011-256122 | 12/2011 |

(Continued)

OTHER PUBLICATIONS

Takashima, Y. et al. "Molecular decoding using luminescence from an entangled porous framework", Nature Communications, Article 168, 2011, 8 pages.

(Continued)

*Primary Examiner* — Taeho Jo
(74) *Attorney, Agent, or Firm* — Oblon, McClelland, Maier & Neustadt, L.L.P.

(57) ABSTRACT

A metal organic framework is configured to emit fluorescence and deform by interaction with a target molecule. The metal organic framework includes: a metal ion; a quadridentate ligand bonded to the metal ion; and a bidentate ligand bonded to the metal ion.

11 Claims, 12 Drawing Sheets

(56) References Cited

U.S. PATENT DOCUMENTS

| | | | | |
|---|---|---|---|---|
| 7,985,868 | B1* | 7/2011 | Bauer | C09K 11/04 |
| | | | | 549/523 |
| 8,367,419 | B2 | 2/2013 | Li et al. | |
| 8,947,756 | B2* | 2/2015 | Noh | C07D 213/53 |
| | | | | 359/265 |
| 9,139,599 | B1* | 9/2015 | Eddaoudi | C07F 1/08 |
| 9,175,211 | B2 | 11/2015 | Xia et al. | |
| 9,492,778 | B1* | 11/2016 | Eddaoudi | B01D 53/04 |
| 2002/0012821 | A1* | 1/2002 | Leddy | B03C 1/01 |
| | | | | 429/10 |
| 2007/0219280 | A1* | 9/2007 | Kitagawa | C07F 1/005 |
| | | | | 520/1 |
| 2010/0170395 | A1* | 7/2010 | Farha | B01D 53/02 |
| | | | | 95/139 |
| 2011/0186124 | A1* | 8/2011 | Agui | H01L 31/022483 |
| | | | | 136/256 |
| 2011/0186125 | A1* | 8/2011 | Agui | H01L 31/022483 |
| | | | | 136/256 |
| 2012/0040471 | A1* | 2/2012 | Chen | C07C 7/12 |
| | | | | 436/172 |
| 2012/0247328 | A1* | 10/2012 | Brown | B01D 53/228 |
| | | | | 95/51 |
| 2012/0289755 | A1* | 11/2012 | Kato | B01D 53/8612 |
| | | | | 588/313 |
| 2013/0060484 | A1* | 3/2013 | Lee | B01J 20/226 |
| | | | | 702/24 |
| 2013/0061752 | A1* | 3/2013 | Farha | B01D 53/02 |
| | | | | 95/139 |
| 2013/0143021 | A1* | 6/2013 | Miller | C08J 3/212 |
| | | | | 428/220 |
| 2014/0106468 | A1* | 4/2014 | Boersma | B82Y 20/00 |
| | | | | 436/501 |
| 2014/0107333 | A1* | 4/2014 | Ma | A61K 31/409 |
| | | | | 540/145 |
| 2014/0179941 | A1* | 6/2014 | Bao | C30B 29/60 |
| | | | | 554/74 |
| 2015/0158013 | A1* | 6/2015 | Eddaoudi | B01J 20/226 |
| | | | | 95/139 |
| 2015/0217268 | A1* | 8/2015 | Farha | B01J 20/226 |
| | | | | 95/139 |
| 2015/0290618 | A1* | 10/2015 | Kajiro | B01J 20/26 |
| | | | | 556/115 |
| 2015/0291641 | A1* | 10/2015 | Zaworotko | C07F 1/08 |
| | | | | 95/139 |
| 2015/0352519 | A1* | 12/2015 | Kim | B01J 20/226 |
| | | | | 206/0.7 |
| 2016/0002421 | A1* | 1/2016 | Dichtel | G01N 33/0057 |
| | | | | 436/98 |
| 2016/0159830 | A1* | 6/2016 | Baceiredo | C07F 15/0086 |
| | | | | 556/12 |
| 2016/0231233 | A1* | 8/2016 | Wang | G01N 21/3504 |
| 2017/0025713 | A1* | 1/2017 | Horai | G01N 31/223 |
| 2017/0040400 | A1* | 2/2017 | Eguchi | H01L 27/12 |
| 2017/0113204 | A1* | 4/2017 | Eddaoudi | B01J 20/226 |
| 2017/0137450 | A1* | 5/2017 | Eddaoudi | C07F 15/045 |
| 2017/0203277 | A1* | 7/2017 | Kim | B01J 20/226 |
| 2017/0227690 | A1* | 8/2017 | Sasaki | C07F 1/08 |
| 2017/0246584 | A1* | 8/2017 | Eddaoudi | B01J 20/28057 |
| 2017/0248051 | A1* | 8/2017 | Eddaoudi | B01J 20/226 |
| 2017/0350225 | A1* | 12/2017 | Benoit | E21B 47/0905 |
| 2018/0011010 | A1* | 1/2018 | Chang | B01J 20/06 |
| 2018/0093218 | A1* | 4/2018 | Eddaoudi | B01J 20/226 |
| 2018/0136379 | A1* | 5/2018 | Takishita | B32B 7/02 |
| 2018/0161755 | A1* | 6/2018 | Matoga | H01M 8/1018 |
| 2018/0164244 | A1* | 6/2018 | Oka | G01N 27/414 |
| 2018/0304246 | A1* | 10/2018 | Eddaoudi | B01J 20/226 |
| 2019/0169376 | A1* | 6/2019 | Hein | C08L 67/00 |

FOREIGN PATENT DOCUMENTS

| | | |
|---|---|---|
| JP | 5017499 | 9/2012 |
| JP | 2016-121160 | 7/2016 |
| WO | WO 2010/042948 A3 | 4/2010 |

OTHER PUBLICATIONS

Farha, O. et al. "Rational Design, Synthesis, Purification, and Activation of Metal-Organic Framework Materials", Accounts of Chemical Research, vol. 43, No. 8, 2010, 10 pages.

Sakata. Y. et al. "Shape-Memory Nanopores Induced in Coordination Frameworks by Crystal Downsizing", Science vol. 339, 2013, 5 pages.

Hu, Z. et al. Selective, Sensitive, and Reversible Detection of Vapor-Phase High Explosives via Two-Dimensional Mapping: A New Strategy for MOF-Based Sensors, Crystal Growth & Design, 2013, 4 pages.

Drache, F. et al. "Vapochromic Luminescence of a Zirconium-Based Metal-Organic Framework for Sensing Applications", European Journal of Inorganic Chemistry, 2016, 7 pages.

\* cited by examiner

FIG.6
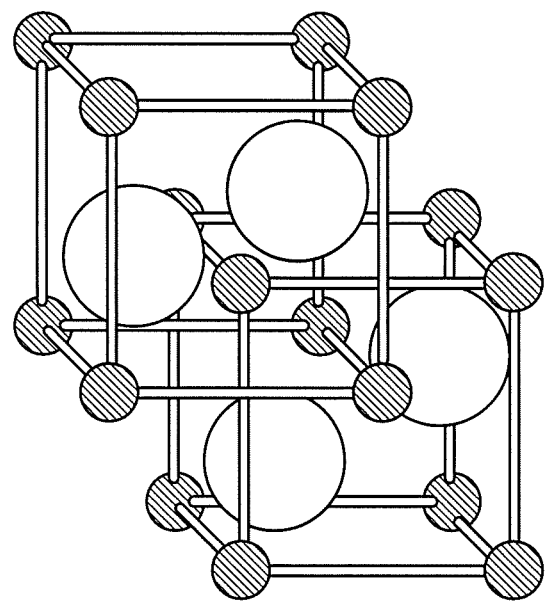
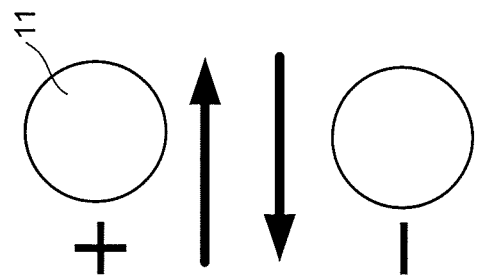
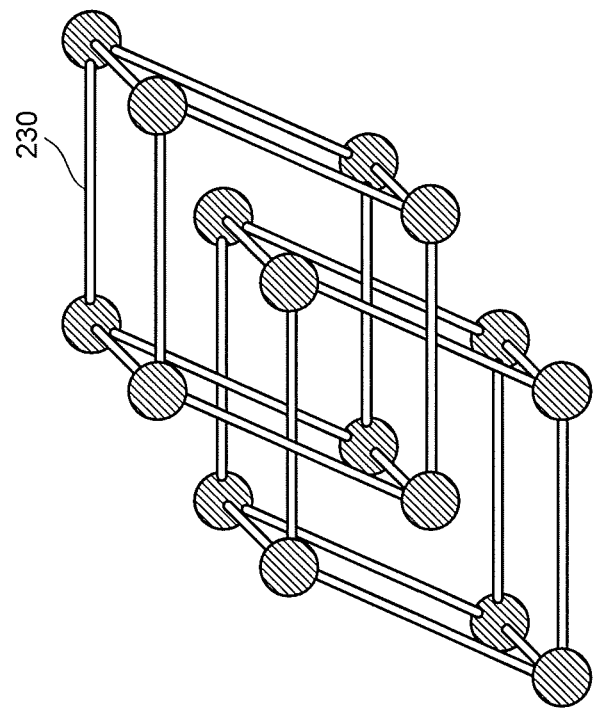

METAL ORGANIC FRAMEWORK, PHOSPHOR FILM, AND MOLECULE DETECTING DEVICE

CROSS REFERENCE TO RELATED APPLICATION

This application is based upon and claims the benefit of priority from Japanese Patent Application No. 2018-053473, filed on Mar. 20, 2018; the entire contents of which are incorporated herein by reference.

FIELD

Embodiments described herein relate generally to a metal organic framework, a phosphor film, and a molecule detecting device.

BACKGROUND

Sensing technology using a smell (gas) sensor is widely used for odor determination, measurement of volatile organic compounds (VOC) in the atmosphere, performance confirmation of air cleaners, trouble detection of devices, and so on because it is capable of digitizing smell in the air.

As a conventional gas sensing method, there are devices such as a flame ionization detector (FID), a photo-ionization detector (PID), and a non-dispersive infra-red (NDIR) gas analyzer. These devices have problems regarding portability, risk due to the use of a flammable gas, life and price of a light source used for the measurement, substance recognition performance, and so on. Therefore, the development of a small sensor advantageous in the assembly in a processing device and the measurement at a work site has been in progress.

As a semiconductor gas sensor which is a small sensor, there has been proposed a sensor that is capable of measuring gas concentration by using a change that electrical properties such as electrical resistance undergo when oxygen adsorbed on porous tin oxide ($SnO_2$) is consumed by a reducing substance. However, a conventionally used oxide semiconductor sensor has several problems regarding detection sensitivity, an operating temperature (300 to 500° C.), durability, gas selectivity, and so on.

BRIEF DESCRIPTION OF THE DRAWINGS

FIG. 6 is a schematic view illustrating a deformation example of the fluorescent MOF.

DETAILED DESCRIPTION

A metal organic framework of an embodiment emits a fluorescence and deforms by interaction with a target molecule. The metal organic framework includes a metal ion, a quadridentate ligand bonded to the metal ion, and a bidentate ligand bonded to the metal ion.

Embodiments will be hereinafter described with reference to the drawings. Note that, in the embodiments, substantially the same constituent parts are denoted by the same reference sign, and a description thereof may be partly skipped. The drawings are schematic, and a relation between the thickness and planar dimension of each part, and a thickness ratio among parts, and so on may be different from actual ones.

Figure 1:
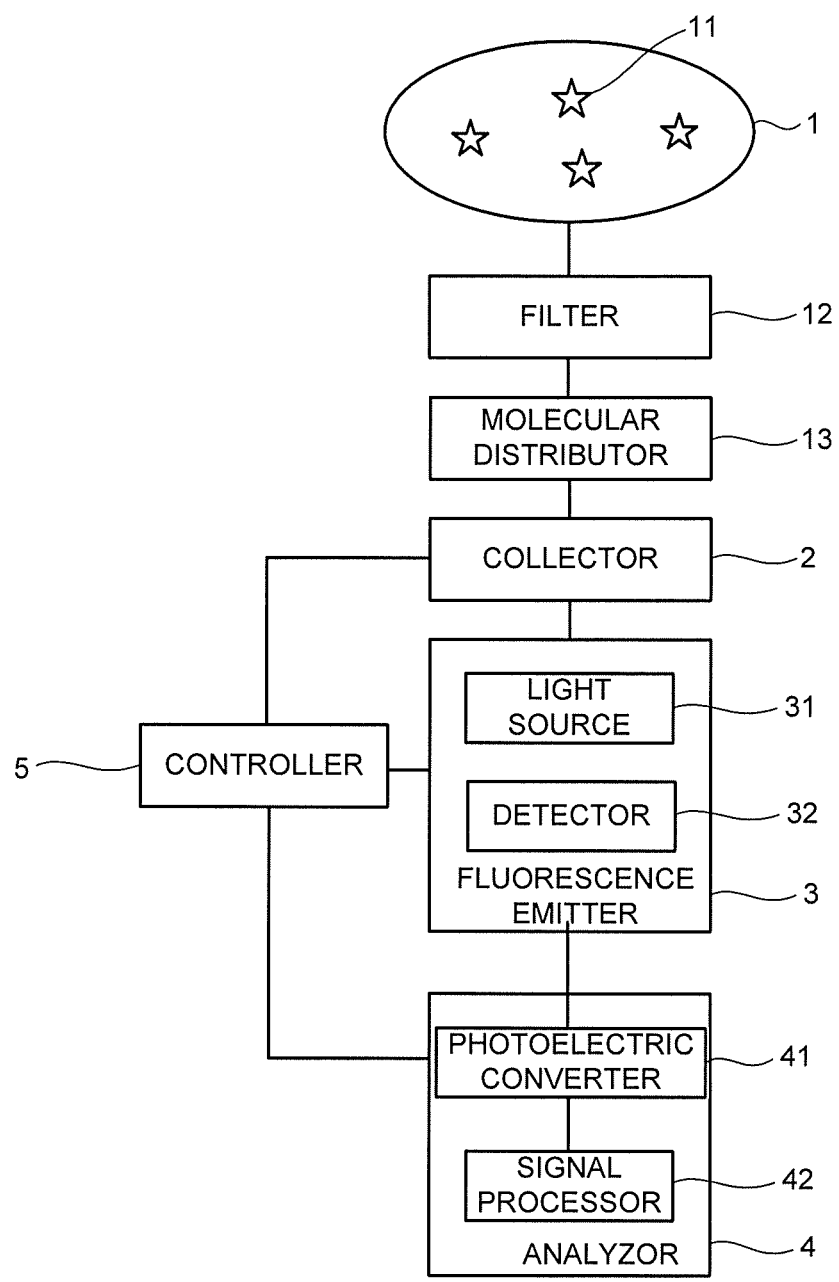
FIG. 1 is a block diagram illustrating a configuration example of a molecule detecting device.

FIG. 1 is a block diagram illustrating a configuration example of a molecule detecting device of an embodiment. The molecule detecting device illustrated in FIG. 1 is a device that detects target molecules (detection targets) 11 in a fluid 1 generated from a gas generating source, for instance, and includes a collector 2, a fluorescence emitter 3, an analyzer 4, and a controller 5.

The collector 2 collects the fluid 1 containing the target molecules 11. The fluid 1 is in a liquid form or a gaseous form. The collector 2 has a collection port for the fluid 1 and connects to a pump through a flow path. The collector 2 may include a filter that removes impurities such as fine particles contained in the fluid 1. Incidentally, a valve may be provided instead of the pump and the start and stop of the introduction of the fluid 1 may be controlled by the opening/closing of the valve.

The fluid 1 may contain, as impurities, a substance having a molecular weight, a molecular structure, and so on similar to the molecular weight, the molecular structure, and so on of the target molecules 11. The target molecules 11 floating in the air are often present as a mixture with various contaminants such as smell components and fine particles. Because of this, the fluid 1 is preferably pre-processed by a filter device 12, a molecular distribution device 13, and so on in advance to be thereafter sent to the collector 2.

As the filter device 12, an ordinary medium/high-efficiency filter or the like is used. In the filter device 12, particulate substances such as fine particles contained in the fluid 1 are removed. The fluid 1 from which the particulate substances have been removed in the filter device 12 is sent to the molecular distribution device 13. The molecular distribution device 13 is, for example, a device that ionizes the fluid 1 into an ionized substance group, applies a voltage to the ionized substance group to cause the ionized substance group to fly at a speed proportional to a mass, and separates ionized substances of the target molecules 11 from the ionized substance group by utilizing the flying speed depending on a mass difference and the time of flight determined by the flying speed. As such a molecular distribution device, a device including an ionizer, a voltage supply, and a time-of-flight separator is used. It should be noted that the filter device 12 and the molecular distribution device 13 do not necessarily have to be provided.

The fluid 1 is collected in the collector 2 as it is or after pre-processed by devices such as the filter device 12 and the molecular distribution device 13. The fluid 1 collected in the collector 2 is sent to the fluorescence emitter 3 through a flow path.

The fluorescence emitter 3 is disposed in the flow path. The fluorescence emitter 3 has a light source 31 that emits light and a detector 32 that emits a fluorescence by being excited by the light and whose fluorescence undergoes a change in an emission spectrum due to an interaction with the target molecules 11.

The analyzer 4 includes: a photoelectric converter 41 that converts the fluorescence from the detector 32 into an electrical signal; and a signal processor 42 that processes the electrical signal from the photoelectric converter 41 to identify the target molecules 11.

The photoelectric converter 41 has a sensor such as, for example, a stand-alone photodiode, or a CMOS image sensor or a SiPM sensor in which a photodiode, MOSFET, wiring, and so on are fabricated on a silicon substrate using well-known ion implantation technology, film-forming technology, or the like. The sensor may be disposed directly or may be disposed indirectly with an optical fiber or the like therebetween. Incidentally, the photoelectric converter 41 may be provided in the fluorescence emitter 3.

The signal processor 42 processes the electrical signal to identify the target molecules 11. The signal processor 42 identifies the target molecules 11 by, for example, comparing a change in the electrical signal before and after the introduction of the fluid 1 and pre-stored electrical signal change data corresponding to the relevant molecules.

The controller 5 electrically connects to the collector 2, the fluorescence emitter 3, and the analyzer 4 and outputs control signals to the respective parts. For example, by means of the control signals, the controller 5 controls the start and stop of the introduction of the fluid 1 to the fluorescence emitter 3 and the start and stop of the irradiation of the light from the light source 31. The controller 5 may further control the identification of the target molecules 11 performed by the signal processor 42, by means of the control signal.

The signal processor 42 and the controller 5 each may be configured, for example, using hardware which uses a processor or the like. Incidentally, the operations may be pre-stored as operating programs in a computer-readable recording medium such as a memory and the operations may be executed by reading the operating programs stored in the recording medium by the hardware when necessary.

Figure 2:
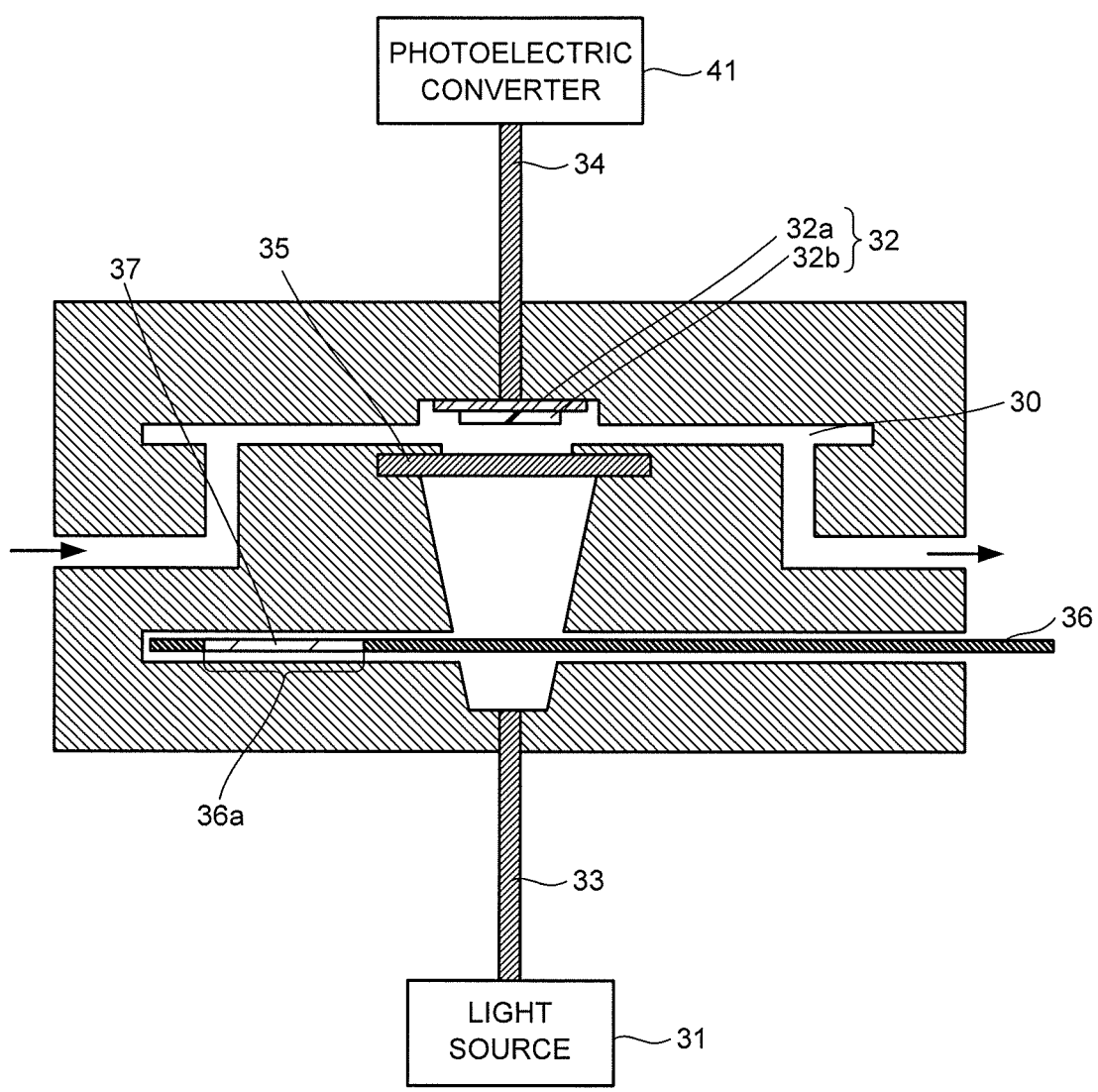
FIG. 2 is a schematic view illustrating a configuration example of a fluorescence emitter.

A configuration example of the fluorescence emitter 3 will be described with reference to FIG. 2. FIG. 2 is a schematic view illustrating the configuration example of the fluorescence emitter 3. The fluorescence emitter 3 includes a measurement flow path 30, the light source 31, the detector 32, optical fibers 33, 34, a diffuser plate 35, and a mechanical shutter 36.

The measurement flow path 30 is space where the fluid 1 flows. The arrows in FIG. 2 indicate a flow direction of the fluid 1. Incidentally, in a case where a valve is provided instead of a pump, the measurement flow path 30 may be pressure-reduced in advance.

The light source 31 may have, for example, an electric bulb, a light-emitting diode, or the like, but is not limited to these. The wavelength of the light from the light source 31 can be appropriately set according to properties of the detector 32. The light from the light source 31 is introduced to the measurement flow path 30 through the optical fiber 33. Incidentally, the light source 31 may be provided in the measurement flow path 30.

The detector 32 has a base 32a and a phosphor film 32b provided on the base 32a. The phosphor film 32b may be attachable/detachable to/from the base 32a when necessary. The detector 32 itself may be attachable/detachable to/from the measurement flow path 30.

As the base 32a, a glass substrate, a polymer film having a high visible light transmittance and not having a fluorescence emission property, or the like is usable, for instance. By using, as the base 32a, a substrate on which a light-transmitting conductive film of an indium tin oxide (ITO) or the like is formed and passing a current thereto, it is possible to heat the base 32a, and owing to the heat, the target molecules 11 adsorbed on the phosphor film 32b are desorbed. This enables the repeated use of the detector 32. It is possible to desorb the target molecules 11 adsorbed on the phosphor film 32b, not only by the above method of forming the light-transmitting conductive film and passing the current but also by providing a heating device or the like that heats the phosphor film 32b.

The phosphor film 32b emits a fluorescence by being excited by the light from the light source 31. The fluorescence from the phosphor film 32b passes through the optical fiber 34 disposed near or in contact with the base 32a to advance to the photoelectric converter 41.

The diffuser plate 35 is provided between the light source 31 and the detector 32. In a case where a point light source such as an LED light source is used as the light source 31, by providing the diffuser plate 35, it is possible to increase a light irradiation area. The diffuser plate 35 does not necessarily have to be provided.

The mechanical shutter 36 has, in its opening portion 36a, an optical filter 37 that cuts visible light. In order to prevent, for example, visible light other than the excitation light from passing through the phosphor film 32b and being detected when the mechanical shutter 36 slides, it is preferable to insert a filter that passes the excitation light but cuts the visible light other than the excitation light.

A filter that selectively cuts the excitation light from the light source 31 may be disposed between the phosphor film 32b and the base 32a or between the base 32a and the photoelectric converter 41, though not illustrated.

A structure example of the phosphor film 32b will be described. The phosphor film 32b has a metal organic framework (MOF) having a fluorescent property. MOF, which is a porous substance having nano-order pores, is capable of holding, in its pores, gas molecules of $H_2$, $CO_2$, and the like at a normal temperature and a normal pressure, and accordingly is used as a gas storage material and a detector of gas molecules, for instance.

Figure 3:
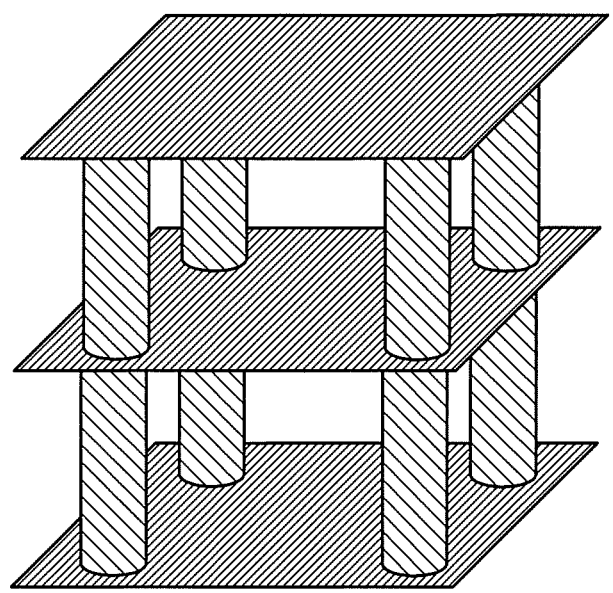
FIG. 3 is a schematic view illustrating an example of pillared layered structures.

As the fluorescent MOF, a fluorescent MOF having, as a detector of the target molecule 11, pillared layered structures illustrated in FIG. 3 is used. FIG. 3 is a schematic view illustrating an example of the pillared layered structures. The pillared layered structure refers to a three-dimensional structure in which a plurality of two-dimensional layer structures each formed of metal ions and first ligands each having a carboxyl group are formed and the layer structures are cross-linked by second ligands each having a pyridyl group, an imidazole group, or an amino group.

The metal ion is not limited, but examples thereof include at least one ion selected from the group consisting of a zirconium ion ($Zr^{4+}$), an aluminum ion ($Al^{3+}$), an iron ion ($Fe^{3+}$), a cobalt ion ($Co^{2+}$), a nickel ion ($Ni^{2+}$), a copper ion ($Cu^{2+}$), a zinc ion ($Zn^{2+}$), and a cadmium ion ($Cd^{2+}$).

Figure 4:
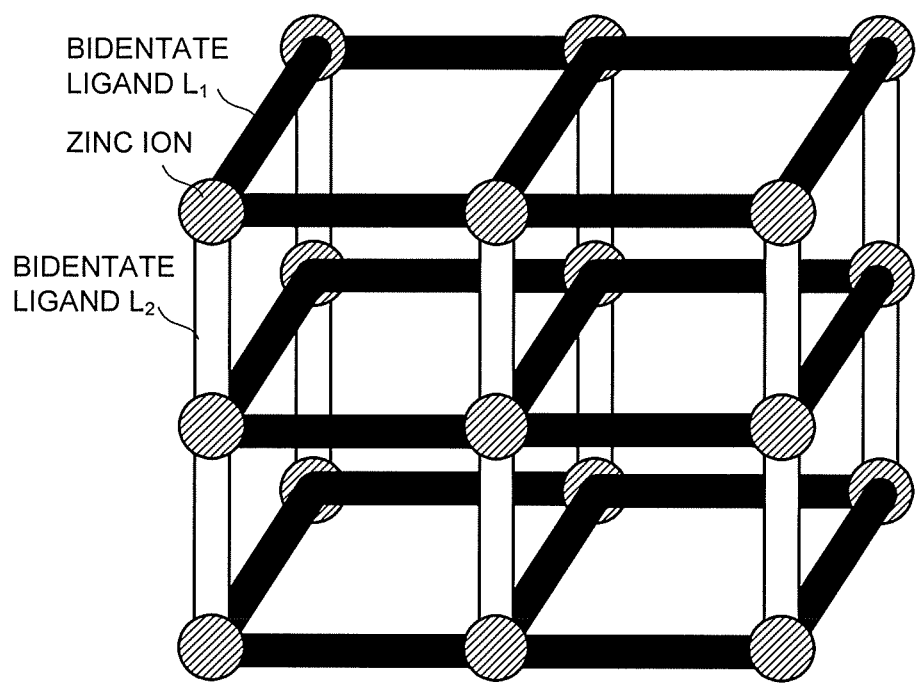
FIG. 4 is a schematic view illustrating a structure example of a fluorescent MOF.

An example of the fluorescent MOF having the pillared layered structures is MOF having zinc ions, carboxylic acid-based bidentate ligands $L_1$ (corresponding to the first ligands) each bonded to the zinc ions, and nitrogen-based bidentate ligands $L_2$ (corresponding to the second ligands) each having a pyridyl group, an imidazole group, an amino group, or the like as illustrated in FIG. 4. The above-mentioned MOF in a state where no solvent or water molecule is coordinated is represented by a general formula:

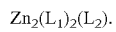

$L_1$ represents at least one bidentate ligand selected from the group consisting of terephthalic acid, 2-amino-terephthalic acid, 2,6-naphthalenedicarboxylic acid, 2,5-furandicarboxylic acid, 2,5-thiophenedicarboxylic acid, 4,4-biphenyldicarboxylic acid, 9,10-anthracenedicarboxylic acid, 2,6-anthracenedicarboxylic acid, 9,10-bis(4-carboxyphenyl)anthracene, 2,7-pyrenedicarboxylic acid, 9-fluorene-2,7-dicarboxylic acid, 9-fluorenone-2,7-dicarboxylic acid, and 4,4'-stilbenedicarboxylic acid.

$L_2$ represents at least one bidentate ligand selected from the group consisting of triethylenediamine, 4,4'-bipyridyl, 1,4-di(4-pyridyl)benzene, 3,6-di(4-pyridyl)-1,2,4,5-tetrazine, 1,2-di(4-pyridyl)ethane, 1,2-di(4-pyridyl)ethylene, and 1,4-bis[(1H-imidazole-1-il)methyl]benzene Ligands that can form a plurality of three dimensional arrangements without destroying the structure is also called flexible ligands. In the aforesaid ligands, especially highly flexible ligands are 4,4'-stilbenedicarboxylic acid as $L_1$, and 1,2-di(4-pyridyl)ethane, 1,2-di(4-pyridyl)ethylene, 1,4-bis[(1H-imidazole-1-il)methyl]benzene as $L_2$. In a fluorescent MOF obtained by the combination of such flexible ligands, unit lattices are capable of flexibly deforming, and in accordance with such deformation, an electron state between the ligands or between the ligands and the metal ions changes due to a π-π interaction or the like, and in some cases, as a result of an additional interaction with guest molecules (corresponding to the target molecules 11), an emission spectrum of the fluorescence is likely to change. For example, an interaction with a nitroaromatic is accompanied by the quench of the fluorescence emission.

Next, a fluorescent MOF having pillared layered structures different from the above-described ones will be described.

Figure 5:
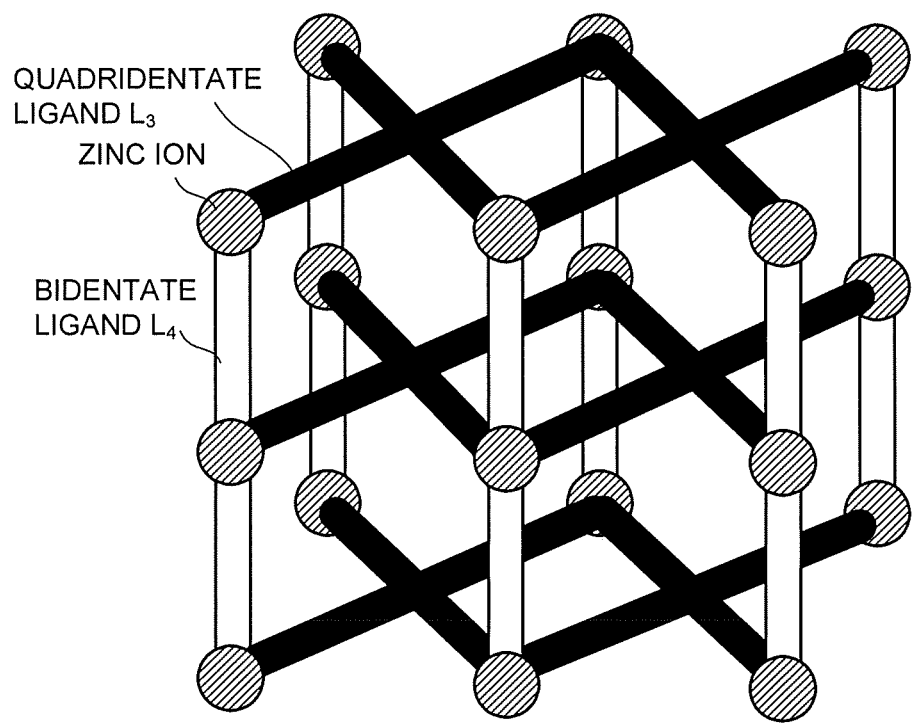
FIG. 5 is a schematic view illustrating a structure example of the fluorescent MOF.

As another example of the fluorescent MOF having the pillared layered structures, there is, for example, a MOF having zinc ions, quadridentate ligands $L_3$ (corresponding to the first ligands) bonded to the zinc ions, and bidentate ligands $L_4$ (corresponding to the second ligands) as illustrated in FIG. 5. The other example of the fluorescent MOF having the pillared layered structures in a state where no solvent or water molecule is coordinated, is represented by a general formula: $Zn_2(L_3)(L_4)$. An emission spectrum of a fluorescence from the fluorescent MOF represented by the general formula: $Zn_2(L_3)(L_4)$ undergoes an especially greater change due to an interaction with the target molecules 11 than the emission spectrum of the fluorescence from the fluorescent MOF represented by the general formula: $Zn_2(L_1)_2(L_2)$.

$L_3$ represents at least one quadridentate ligand selected from the group consisting of 1,2,4,5-tetrakis(4-carboxyphenyl)benzene, 1,2,4,5-tetrakis(4'-carboxy[1,1'-biphenyl]-4-il)benzene, tetrakis(4-carboxyphenyl)ethylene, tetrakis(4'-carboxy[1,1'-biphenyl]-4-il)ethylene, 3,3',5,5'-tetra(4-carboxyphenyl)biphenyl, N,N,N',N'-tetrakis(4-carboxyphenyl)-biphenyl-4,4'-diamine, 1,3,6,8-tetra(4-carboxyphenyl)pyrene, and tetrakis(4-carboxyphenyl)porphyrin. In these quadridentate ligands, even in a state where the four carboxyl groups and the metal ions are bonded, an angle of bonds extending radially changes flexibly like a hinge, and the electron state between the ligands or between the ligands and the metal ions changes, which is thought to change the fluorescence emission spectrum as a result.

Regarding, for example, 1,2,4,5-tetrakis(4-carboxyphenyl)benzene, a calculation example of potential energy of the rotation of a benzene ring of a side chain is given below. Hereinafter, 1,2,4,5-tetrakis(4-carboxyphenyl)benzene will be abbreviated to TCPB. The structure and rotation energy of a TCPB molecule are found by calculation based on a density functional theory (DFT) using the correction of Becke's three-parameter exchange potential and Lee-Yang-Parr correlation potential (B3YP). The free rotation of the molecule in a case of independent TCPB is expressed by performing structure optimization calculation on the total freedom using a 6-31+G(d, p) basis function including d- and hydrogen p-polarization functions and a diffuse function, and calculating the rotation potential energy of the benzene ring of the side chain. Regarding the rotation of the molecule in a case where TCPB is incorporated in the MOF structure, the structure of the TCPB molecule bonded to the metals is extracted using a cep-31G basis of effective core potential (ECP)+Double Zeta (DZ), and under a condition where end portions are terminated with H and the positions of —COOH at four corners are fixed, the rotation potential energy of the benzene ring of the side chain is calculated using 6-31+G(d, p) basis. All the calculations can be performed using a molecular orbital calculation program Gaussian 16. As a result of such calculations, the rotation potential energy of the benzene ring of the side chain in the case of the independent TCPB molecule is 6.6 kcal/mol. On the other hand, the rotation potential energy of the benzene ring of the side chain in the case where TCPB is assumed to be incorporated in the MOF structure and bonded to the metals is 12.5 kcal/mol. That is, it is seen that the benzene ring of the side chain of the TCPB molecule has potential energy small enough to sufficiently rotate at a room temperature even in the case where TCPB is incorporated in the MOF structure, not to mention the case where it is in the independent state. Similarly to this example, aromatic rings of bonds extending radially, of the quadridentate ligands are thought to be rotatable at the room temperature, and this axis rotation is restrained by the guest molecules, which as a result contributes to the change in the emission intensity.

$L_4$ represents at least one bidentate ligand selected from the group consisting of triethylenediamine, 4,4'-bipyridyl, 1,4-di(4-pyridyl)benzene, 3,6-di(4-pyridyl)-1,2,4,5-tetrazine, 1,2-di(4-pyridyl)ethane, 1,2-di(4-pyridyl)ethylene, and 1,4-bis[(1H-imidazole-1-il)methyl]benzene. Among the above bidentate ligands, bidentate ligands especially high in flexibility are 1,2-di(4-pyridyl)ethane, 1,2-di(4-pyridyl)ethylene, and 1,4-bis[(1H-imidazole-1-il)methyl]benzene.

In such a fluorescent MOF, the unit lattices are flexibly deformable, and in accordance with the deformation, an electron state between the ligands or between the ligands and the metal ions changes, and in some cases, due to an additional interaction with the guest molecules, the fluorescence emission spectrum is as a result likely to change.

FIG. 6 is an explanatory schematic view of a deformation example of the fluorescent MOF having the pillared layered structures illustrated in FIG. 4. The fluorescent MOF having the pillared layered structures often has a structure in which unit lattices 230 of the fluorescent MOF are catenated in a chain form as illustrated in FIG. 6. In the case where the unit lattices are catenated, the target molecules 11 are sandwiched between the adjacent ligands, and as a result, the lattices of the fluorescent MOF deform, resulting in a change in lattice interval.

Figure 7:
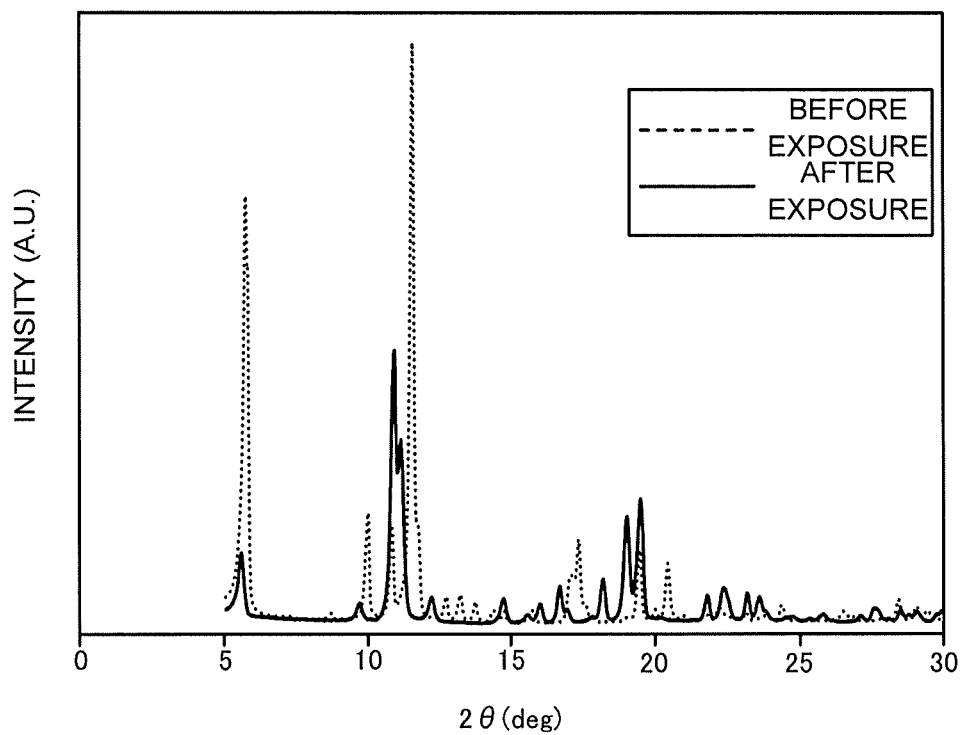
FIG. 7 is a chart illustrating an example of X-ray diffraction patterns of a fluorescent MOF.

The above-described deformation and change in the lattice interval can be confirmed from, for example, an X-ray diffraction (XRD) pattern. FIG. 7 is an example of X-ray diffraction patterns of a fluorescent MOF having the pillared layered structures. In FIG. 7, a fluorescent MOF having zinc ions, 2-4,5-tetrakis(4-carboxyphenyl)benzene being the quadridentate ligands, and 1,2-di(4-pyridyl)ethylene being the bidentate ligands is used, and X-ray diffraction patterns before and after the exposure to saturated vapor of heptane are illustrated. For example, a peak corresponding to 2θ=5.7 degrees at which the intensity is highest and a 15.5-angstrom lattice interval before the heptane exposure almost completely disappears after the heptane exposure, and a peak corresponding to 2θ=11 degrees and an 8-angstrom lattice interval is strong. That is, it is seen that the interval of the unit lattices of the fluorescent MOF having the pillared layered structures greatly changes due to the heptane adsorption.

In the example given here, $L_3$ being the quadridentate ligands are ligands each having a carboxyl group at an end, and $L_4$ being the bidentate ligands are ligands each having a nitrogen-based substituent such as a pyridyl group, an imidazole group, or an amino group at an end, but conversely, $L_3$ may be the ligands each having the nitrogen-based substituent such as the pyridyl group, the imidazole group, or the amino group at the end and $L_4$ may be the ligands each having the carboxyl group at the end.

The fluorescent MOF having the pillared layered structures as described above emits the fluorescence by being excited by the light from the light source 31 and also deforms due to the interaction with the target molecules 11 which are the guest molecules. The emission spectrum of the fluorescence from the fluorescent MOF changes in accordance with this deformation. By using the above phenomenon, it is possible to constitute a molecule detecting device such as, for example, a VOC sensor and an explosive sensor. The change in the emission spectrum may include not only a difference from a parameter such as emission intensity of the emission spectrum before the fluid 1 is introduced but also a temporal change in a parameter of the emission spectrum when the fluid 1 is introduced for a predetermined period.

Even in a case where the number of the target molecules 11 is very small, the fluorescent MOF having the pillared layered structures is capable of taking the target molecules 11 into its pores and concentrating them, and thus is capable of detecting the target molecules 11 with high sensitivity. Further, since the adsorbed target molecules 11 can be removed by heating or pressure-reduction, the detector 32 is repeatedly usable. The fluorescent MOF having the pillared layered structures is capable of interacting in a gas phase without using a solution or a solvent.

Many MOFs have high heat resistance because they are not decomposed even if being heated to 300° C. or higher. On the other hand, the fluorescent MOF used in the phosphor film 32b is typically in a particulate form containing particles with a particle size of not less than 10 nm nor more than 100 μm, and in order for it to actually function as the detector 32, it is preferable to make MOF adhere to an adhesive material or to disperse MOF in a medium having a light transmitting property to form a film. Consequently, the detector 32 keeps a stable shape and is repeatedly usable.

In order to prevent unnecessary desorption or peeling of the fluorescent MOF particles due to the exposure to the fluid 1, the fluorescent MOF particles are more preferably dispersed in a matrix having a light-transmitting polymer. The polymer in which the fluorescent MOF particles are dispersed preferably has a high permeability for the fluid 1 because the target molecules 11 need to diffuse in the polymer to reach the fluorescent MOF particles. Specifically, permeabilities for gases of $CO_2$, $N_2$, $O_2$, $CH_4$, and $H_2$ at a room temperature are all $10 \times 10^{-10}$ ($cm^3$ (STP) $cm/cm^2 \cdot s \cdot cmHg$) or more, and more preferably $100 \times 10^{-10}$ ($cm^3$ (STP) $cm/cm^2 \cdot s \cdot cmHg$) or more.

Preferably, the polymer in which the fluorescent MOF is dispersed is high in transmittance for light in an excitation wavelength region and an emission wavelength region of the fluorescent MOF, and is high in durability against the light in the aforesaid wavelength regions. In order not to impair the function as the phosphor film 32b, the transmittance for light in a peak excitation wavelength and a peak emission wavelength of the fluorescent MOF is preferably 50% or more, and more preferably 70% or more.

As described above, the fluorescent MOF readily deforms because it has the flexible pillared layered structures. When such a fluorescent MOF is dispersed in a high-rigidity matrix, a change in the emission spectrum caused by the target molecules 11 is restrained, which may deteriorate the detection sensitivity. On the other hand, in order to desorb the adsorbed target molecules 11 from the fluorescent MOF to enable the repeated use, 100° C. to 200° C. heating is effective, but in a case where a thermoplastic polymer not having rubber elasticity is used, the heat causes a molecular chain to flow, which in turn changes a dispersion state of the fluorescent MOF, though only slightly. In the application to the detector 32 which detects a small change in the fluorescence emission spectrum, the aforesaid film quality change has to be avoided. Therefore, as the polymer in which the fluorescent MOF is dispersed, it is necessary to select a material that is flexible, has rubber elasticity, returns to the original state even if deforming, and has excellent heat resistance. Therefore, the polymer is preferably a polymer having a glass transition temperature of a room temperature or lower, and more preferably −50° C. or lower, having rubber elasticity, and having a heat resistant temperature of 100° C. or higher, and more preferably 150° C. or higher.

The matrix in which the fluorescent MOF is dispersed is preferably a silicone polymer whose main component is alkylsiloxane. Not only the silicone polymer simply disperses the fluorescent MOF in the matrix, but also an alkylsilanol group and an alkoxysilyl group present in a precursor of the silicone polymer interact with the metal ions constituting the fluorescent MOF. Further, the aforesaid interaction of the fluorescent MOF and the silicone polymer makes the film quality change such as the aggregation and desorption of the fluorescent MOF particles in the matrix difficult to occur. This is important in the application to a sensor that detects a slight change in the fluorescence emission spectrum. Further, at the time of the heating intended to desorb the target molecules 11 from the phosphor film 32b, some combination of MOF and a silicone material sometimes have heat resistance higher than those of the respective materials.

A silicone material is especially high in gas permeability and does not inhibit the diffusion of the target molecules 11 into the matrix. Further, the silicon material allows water vapor to permeate but has water repellency against bulk water. For example, in a case where a substance contained in water is to be detected, since the fluorescent MOF in the silicone matrix is not exposed to bulk water, even a fluorescent MOF material that is poor in durability (easily undergoes ionic dissociation) in water is usable. In order to form such a phosphor film 32b, an ordinary liquid silicone polymer is used, the fluorescent MOF is mixed before the silicone polymer is cured or at a stage where it is half-cured, and the resultant is applied into an appropriate thickness and shape and is cured. As the liquid silicone polymer, a commercially available one-component condensation type, two-component condensation type, one-component addition type, two-component addition type, or the like is usable. As its coating method, mask coating, screen printing, spin coating, and other ordinary typical coating/printing method is usable.

The thickness of the phosphor film 32b is not limited, but if it is less than 100 nm, sufficient fluorescence intensity may not be obtained, and if it is over 500 μm, it takes a long time for the target molecules 11 to diffuse in the film, and a response speed is sacrificed, and therefore, the thickness is preferably within a range of not less than 100 nm nor more than 500 μm.

Next, an example of a molecule detection method using the molecule detecting device will be described. Based on the control signals from the controller 5, the fluid 1 being a detection target is introduced to the measurement flow path 30 from the collector 2, and at the same time, the detector 32 is irradiated with the light by the light source 31. When the fluorescence excited by the light from the light source 31 is sent from the detector 32 to enter the photoelectric converter 41, the electrical signal is generated. A value of the electrical signal changes as the emission spectrum of the fluorescence changes due to the interaction between the metal organic framework and the target molecules 11.

Thereafter, the signal processor 42 processes the electrical signal and compares the pre-stored data and the data of this electrical signal to identify the target molecules 11 detected in the fluorescence emitter 3.

As described above, the molecule detecting device of the embodiment can have improved detection sensitivity to the target molecules by including the detector using the fluorescent MOF having the flexible pillared layered structures. Further, since the fluorescent MOF interacts with a plurality of kinds of target molecules, it is also possible to improve detection selectivity.

EXAMPLES (Synthesis of MOF-A)

0.64 g 2,6-naphthalenecarboxylic acid, 0.27 g 1,2-di(4-pyridyl)ethylene, and 0.87 g zinc nitrate hexahydrate were dissolved in a 120 mL dimethylformamide (DMF) solvent. The mixture was put into a 200 ml three-necked flask equipped with a Dimroth condenser, and heated and stirred for six hours while a set temperature of an oil bath was controlled such that the temperature of the solution became 140° C. When a solid component settled, the temperature was lowered, and the mixture was left standing still for a while, and thereafter, a solvent component as a supernatant liquid was removed (decanted). The remaining solid component was cleaned with DMF several times and filtered. After the cleaning, it was dried on a filter paper at a room temperature for 24 hours in the atmosphere. Consequently, MOF ([$Zn_2(ndc)_2(bpee)$]·$2.25DMF·0.5H_2O$), which is a white solid, was obtained.

(Synthesis of MOF-B)

0.51 g 1,2,4,5-tetrakis(4-carboxyphenyl)benzene, 0.17 g 1,2-di(4-pyridyl)ethylene, and 0.54 g zinc nitrate hexahydrate were dissolved in a 100 mL dimethylformamide (DMF) solvent. The mixture was put into a 200 ml three-necked flask equipped with a Dimroth condenser, and heated and stirred for six hours while a set temperature of an oil bath was controlled such that the temperature of the solution became 140° C. When a solid component settled, the temperature was lowered, and the mixture was left standing still for a while, and thereafter, a solvent component as a supernatant liquid was removed (decanted). The remaining solid component was cleaned with DMF several times. It was immersed in methanol and was left at a room temperature for several days. The solid was recovered by filtering. The recovered solid was vacuum-dried using a dry ice trap. Consequently, MOF ($Zn_2(tcpb)(bpee)$), which is a white solid, was obtained.

(First Method of Producing Phosphor Film)

20 mg of MOF was weighed and put on a Teflon petri dish in a $N_2$ glove box, and 180 mg one-component condensation type silicone (TN3305 manufactured by Momentive Performance Materials) was added thereto and quickly mixed by a dispersing spoon so that the whole became uniformly milk white. This MOF-dispersed silicone was applied on a 15 mm quartz substrate to be shaped, using an about 80 μm-thick Teflon film having circular holes with a 10 mm diameter as a mask. Thereafter, the resultant was taken out of the glove box and was cured at a room temperature for three days in the atmosphere. After the MOF-dispersed silicone film was completely cured, the mask was removed, and the whole was immersed in methanol for one hour, and a low-molecular component in the MOF-silicone hybrid film was eluted. Next, it was vacuum-dried for three hours while heated to 120° C., for the initialization. Thereafter, it was kept in the $N_2$ glove box until the measurement time.

(Second Method of Producing Phosphor Film)

10 mg of MOF was weighed and put on a Teflon petri dish in a $N_2$ glove box, and 190 mg one-component condensation type silicone (TSE389 manufactured by Momentive Performance Materials) was added thereto and quickly mixed by a dispersing spoon so that the whole became uniformly milk white. Using this MOF-dispersed silicone, a thin film with an about 30 μm thickness was applied on a light-transmitting nylon film with a 100 thickness by an applicator. Immediately thereafter, the resultant was taken out of the glove box and was cured at a room temperature for three days in the atmosphere. After the MOF-dispersed silicone film was completely cured, it was vacuum-dried for three hours while heated to 100° C., for the initialization. Thereafter, it was cut to 15 mm and kept in the $N_2$ glove box until the measurement time.

Example 1

Figure 8:
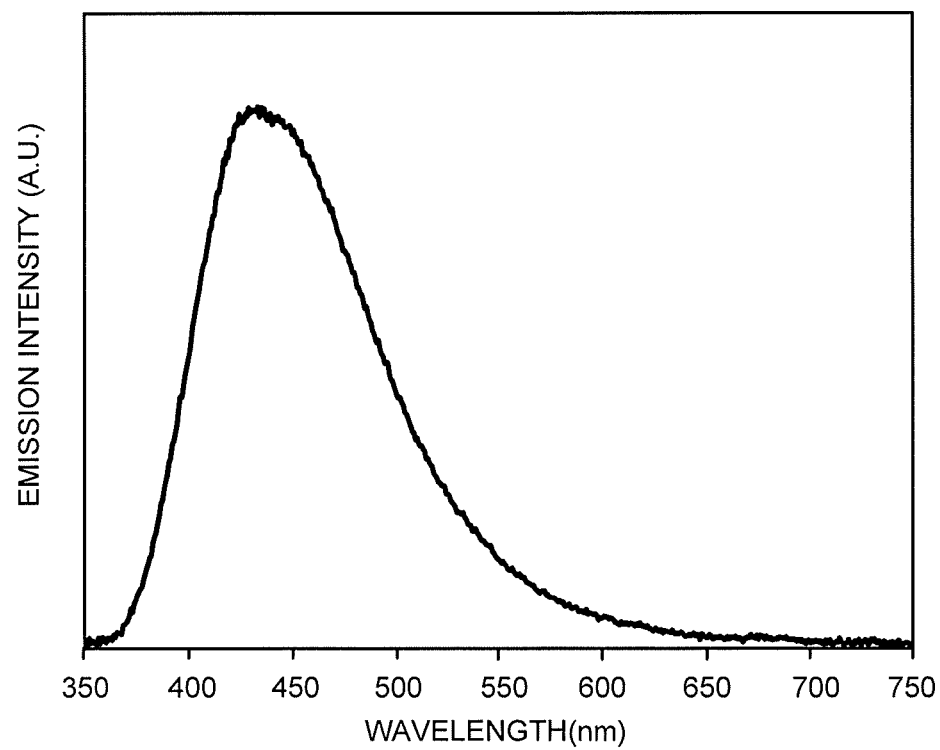
FIG. 8 is a chart illustrating an example of an emission spectrum.

A base having the phosphor film which was fabricated by the first production method using MOF-A was prepared. FIG. 8 illustrates an emission spectrum of a fluorescence when the phosphor film was excited by a 300 nm wavelength light. Next, the base having the phosphor film was set in a fluorescence emitter. A light source was UV-LED whose center wavelength was 300 nm, and a UV-resistant optical fiber was used. Further, as a UV-pass visible-cut filter that passes wavelengths of 380 nm or lower and cuts higher wavelengths, U-340 manufactured by HOYA CANDEO OPTRONICS was used, and the phosphor film was uniformly irradiated with diffused light having passed through the light diffuser plate. The similar optical fiber to an optical fiber used for the light source was used on a photoelectric conversion side. A fluorescence obtained from the phosphor film through the optical fiber passed through SC-39, which is a UV-cut visible-pass filter manufactured by FUJIFILM CORPORATION, disposed in the photoelectric converter including an avalanche photodiode, signal processing for reducing noise was performed, and a temporal change in fluorescence intensity was recorded.

Figure 9:
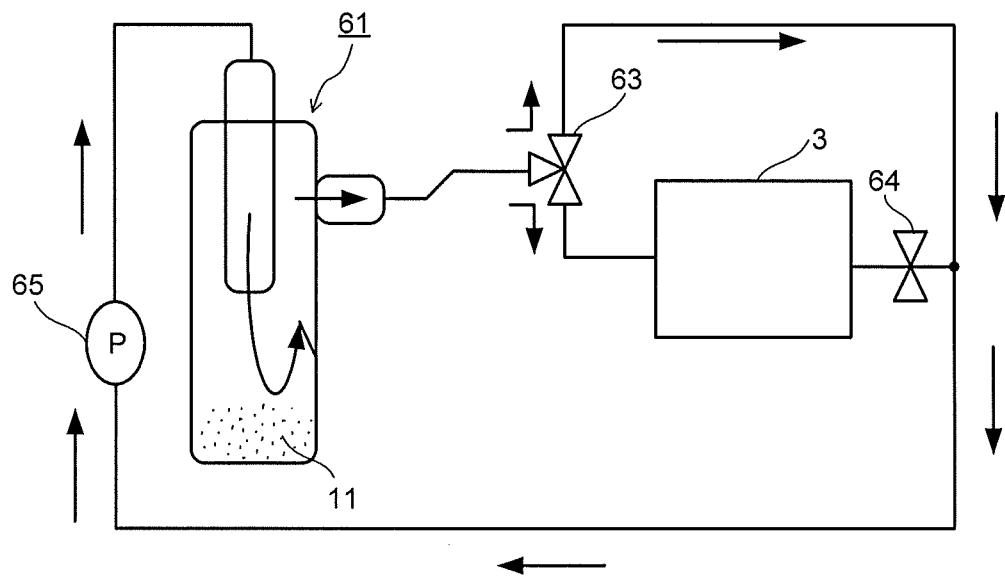
FIG. 9 is a diagram illustrating the configuration of a measurement system.
Figure 10:
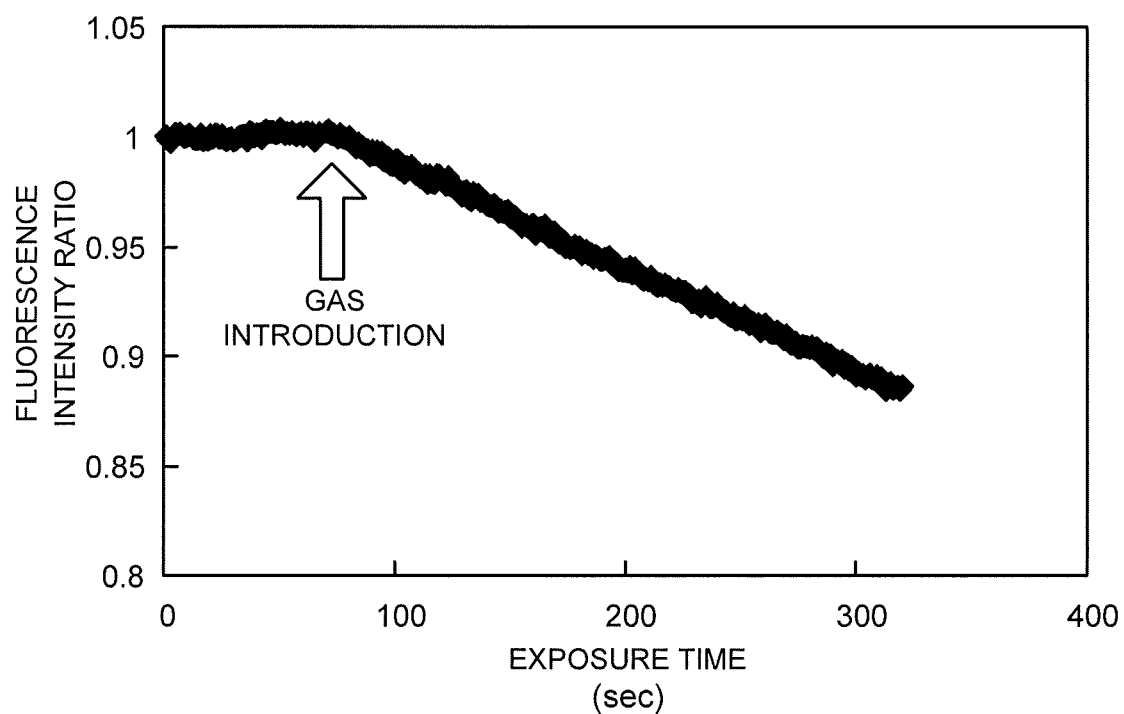
FIG. 10 is a chart illustrating a temporal change in fluorescence intensity.

FIG. 9 is a diagram illustrating a configuration example of a measurement system. The measurement system illustrated in FIG. 9 includes a gas generating device 61, a fluorescence emitter 3, a three-way valve 63, a valve 64, and a pump 65. As the gas generating device 61, a glass instrument with a 30 ml internal volume called an impinger was used. A detection target solid or liquid is weighed and put into the impinger, and a predetermined volume of air was sent thereto along with the suction by the pump 65, whereby a gas containing the target molecules 11 is generated. In this example, a 1 g 4-nitrotoluene powder was used, and the gas was circulated at a 1 L/min flow rate. The gas was prevented from passing through the fluorescence emitter by the three-way valve 63 and the valve 64 for a predetermined time, and after the gas concentration was stabilized, the three-way valve 63 was switched over to send the gas to the fluorescence emitter 3, and a temporal change in a fluorescence intensity ratio relative to the initial intensity was measured. FIG. 10 illustrates the result. It is seen that it is possible to detect the 4-nitrotoluene by thus measuring the temporal change in the fluorescence intensity.

Example 2

Figure 11:
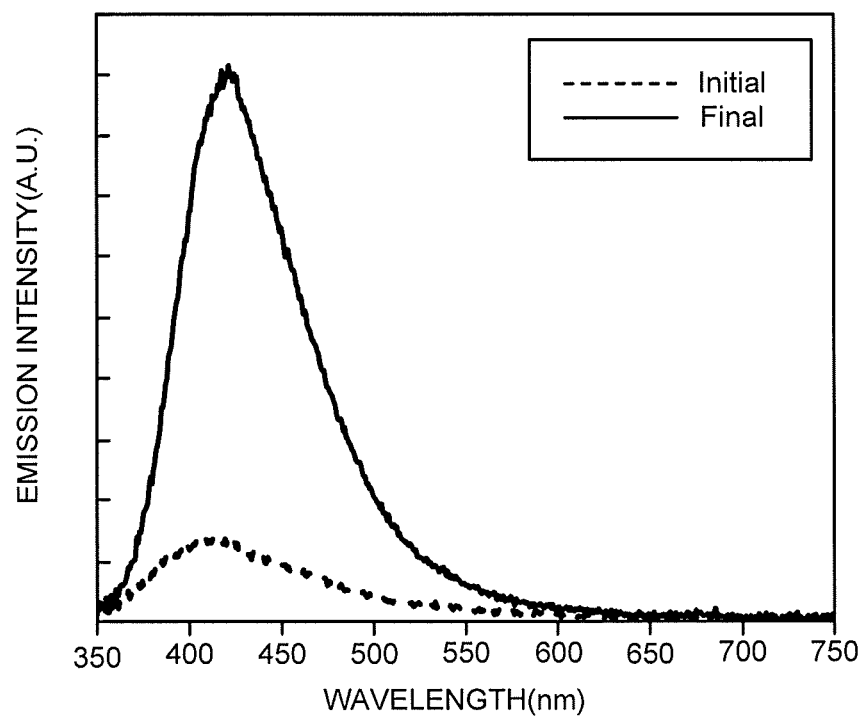
FIG. 11 is a chart illustrating a change in an emission spectrum due to toluene exposure.
Figure 12:
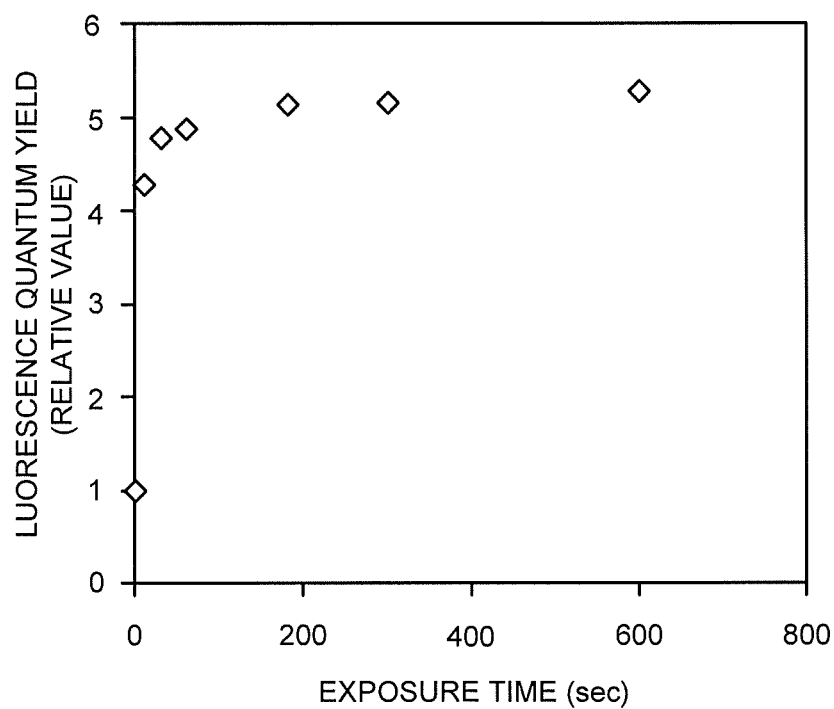
FIG. 12 is a chart illustrating a temporal change in a fluorescence quantum yield due to the toluene exposure.

A base having the phosphor film which was fabricated by the second production method using MOF-B was prepared. Next, a simple gas detection evaluation experiment using this base was conducted. First, a 1 g detection target solid or liquid was weighed and put into a 20 ml glass sample bottle. Next, the base was placed on the sample bottle, with the phosphor film facing downward, so as to completely cover an opening of the sample bottle. In this state, it was exposed to vapor of the detection target that naturally diffuses in the sample bottle at a normal temperature and a normal pressure. This was set in a photometric quantity evaluation and spectrometry system manufactured by Hamamatsu Photonics K.K, and a change in an emission spectrum of a fluorescence was recorded, with the cumulative exposure time being set to, for example, 10 seconds, 30 seconds, 60 seconds, 180 seconds, 300 seconds, and 600 seconds, for instance. In this example, toluene was used and an excitation wavelength was set to 300 nm. FIG. 11 illustrates an initial emission spectrum (Initial) of a fluorescence and its emission spectrum when 600 seconds passed after the toluene vapor exposure (Final). Further, FIG. 12 illustrates relative values of a fluorescence quantum yield with respect to its initial value. It is seen from FIG. 11 and FIG. 12 that the toluene can be detected from a change in the emission spectrum.

Example 3

Figure 13:
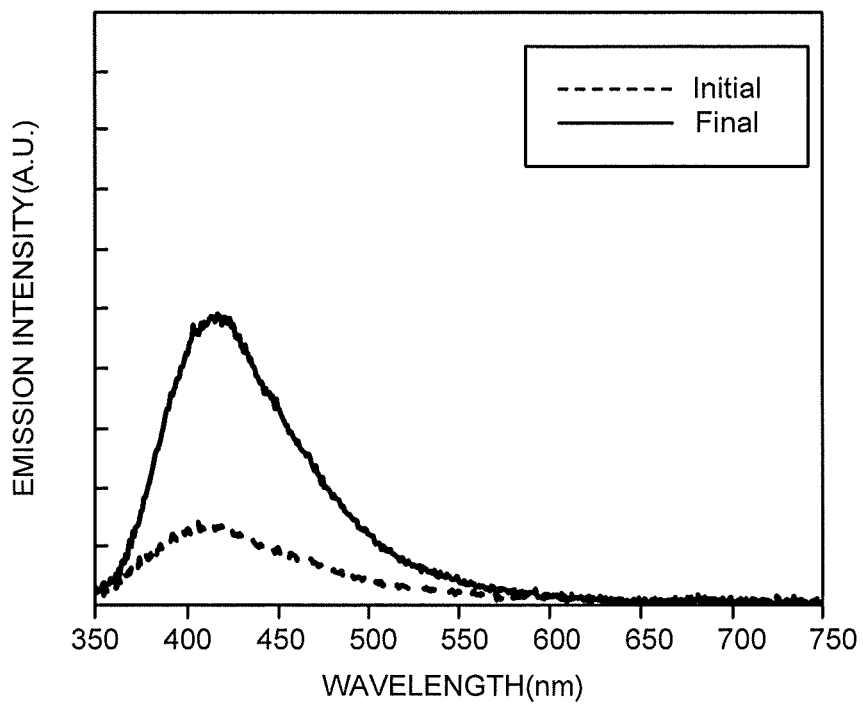
FIG. 13 is a chart illustrating a change in an emission spectrum due to heptane exposure.
Figure 14:
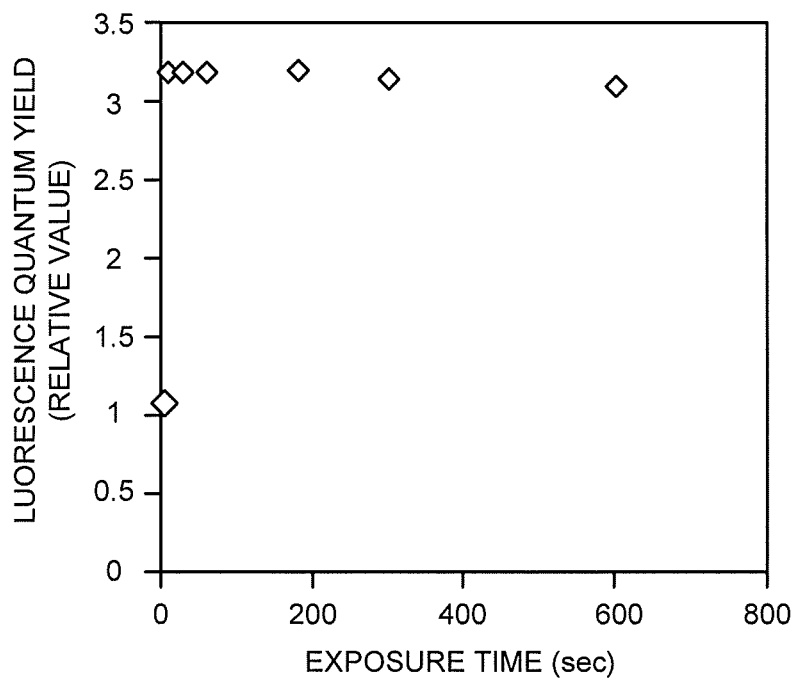
FIG. 14 is a chart illustrating a temporal change in a fluorescence quantum yield due to the heptane exposure.

An evaluation was conducted by the same method as in Example 2 except that the detection target was changed to heptane. FIG. 13 illustrates an initial emission spectrum (Initial) of a fluorescence and its emission spectrum when 600 seconds passed after the heptane vapor exposure (Final). Further, FIG. 14 illustrates relative values of a fluorescence quantum yield with respect to its initial value. It is seen from FIG. 13 and FIG. 14 that it is possible to detect the heptane by measuring a change in the emission spectrum.

Example 4

Figure 15:
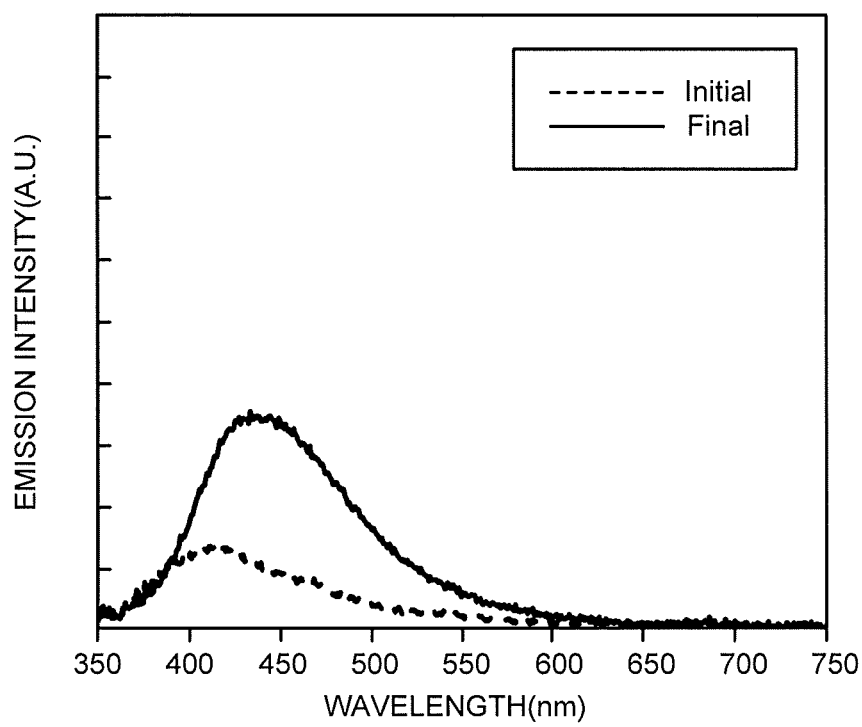
FIG. 15 is a chart illustrating a change in an emission spectrum due to chloroform exposure.
Figure 16:
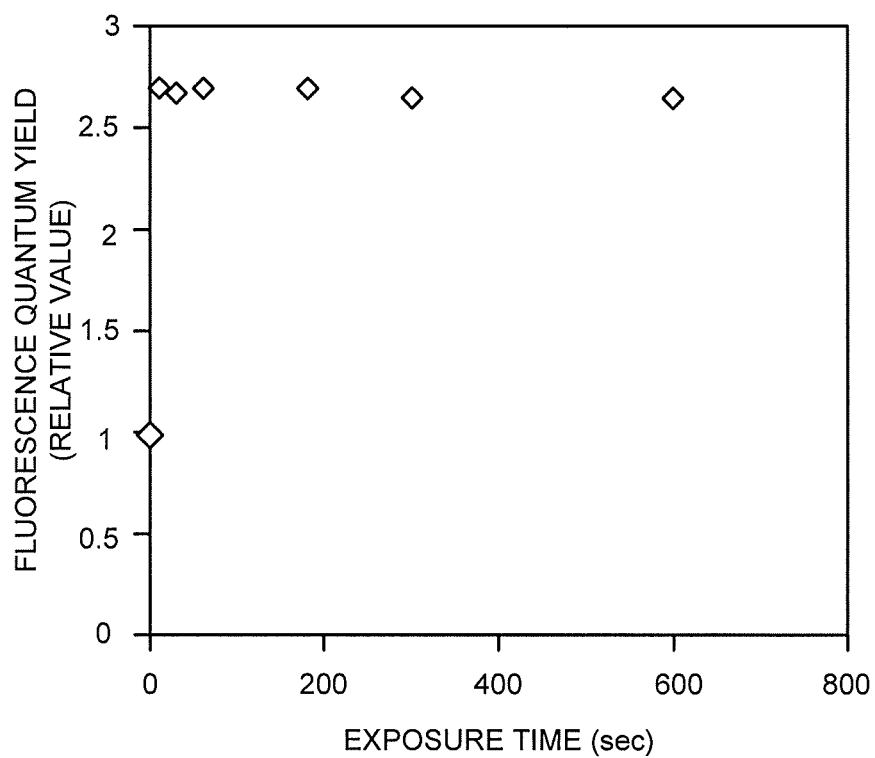
FIG. 16 is a chart illustrating a temporal change in a fluorescence quantum yield due to the chloroform exposure.

An evaluation was conducted by the same method as in Example 2 except that the detection target was changed to chloroform. FIG. 15 illustrates an initial emission spectrum (Initial) of a fluorescence and its emission spectrum when 600 seconds passed after the chloroform vapor exposure (Final). Further, FIG. 16 illustrates relative values of a fluorescence quantum yield with respect to its initial value. It is seen from FIG. 15 and FIG. 16 that it is possible to detect the chloroform by measuring a change in the emission spectrum.

Example 5

Figure 17:
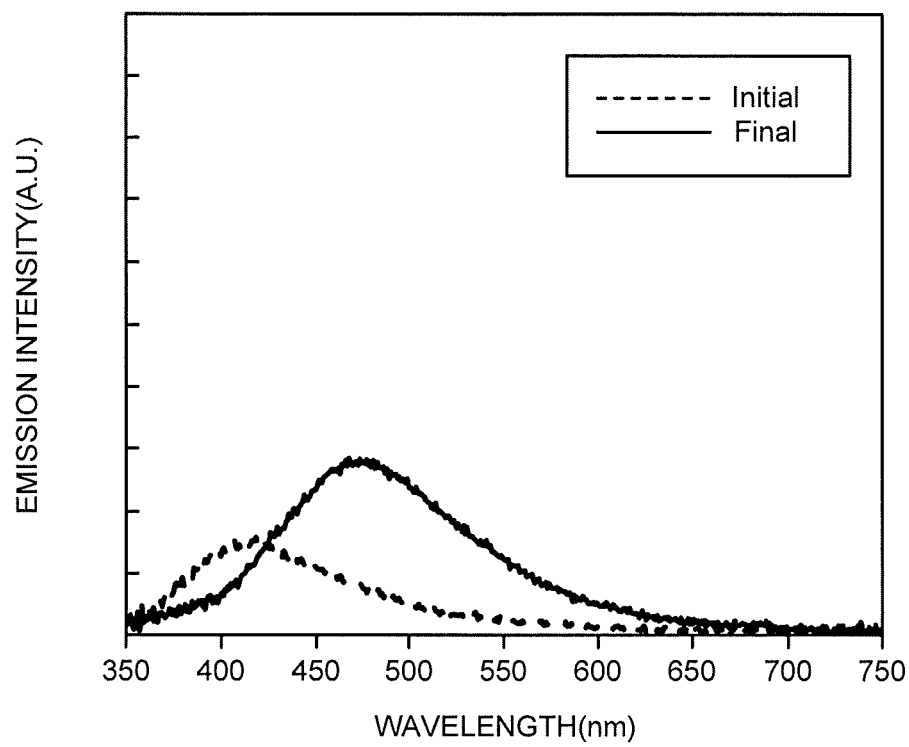
FIG. 17 is a chart illustrating a change in an emission spectrum due to acetone exposure.
Figure 18:
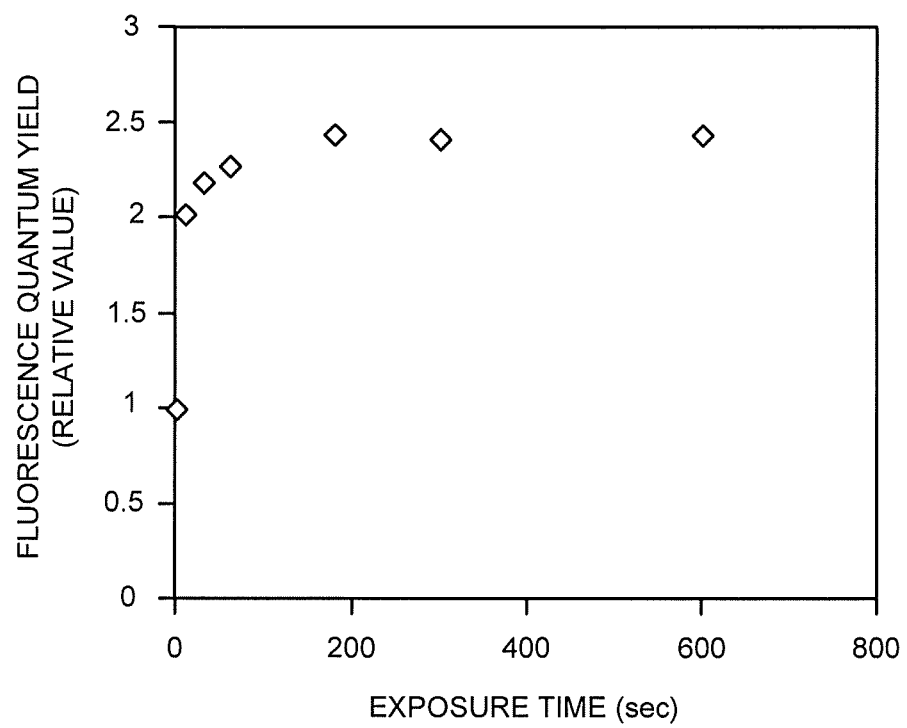
FIG. 18 is a chart illustrating a temporal change in a fluorescence quantum yield due to the acetone exposure.

An evaluation was conducted by the same method as in Example 2 except that the detection target was changed to acetone. FIG. 17 illustrates an initial emission spectrum (Initial) of a fluorescence and its emission spectrum when 600 seconds passed after the acetone vapor exposure (Final). Further, FIG. 18 illustrates relative values of a fluorescence quantum yield with respect to its initial value. It is seen from FIG. 17 and FIG. 18 that it is possible to detect the acetone by measuring a change in the emission spectrum.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A phosphor film, comprising:
a matrix that comprises alkylsiloxane and allows a target molecule to permeate therethrough; and
a metal organic framework configured to emit a fluorescence and deform by interaction with the target molecule.

2. The phosphor film of claim 1,
wherein the metal organic framework comprises:
a metal ion;
a quadridentate ligand bonded to the metal ion; and
a bidentate ligand bonded to the metal ion.

3. The phosphor film according to claim 2, wherein the metal ion is at least one ion selected from the group consisting of a zirconium ion, an aluminum ion, an iron ion, a cobalt ion, a nickel ion, a copper ion, a zinc ion, and a cadmium ion.

4. The phosphor film according to claim 2, wherein the quadridentate ligand has a carboxyl group, and the bidentate ligand has a pyridyl group, an imidazole group, or an amino group.

5. The phosphor film according to claim 2, wherein the quadridentate ligand is at least one ligand selected from group consisting of
1,2,4,5-tetrakis(4-carboxyphenyl)benzene, 1,2,4,5-tetrakis(4'-carboxy[1,1'-biphenyl]-4-il)benzene,
tetrakis(4-carboxyphenyl)ethylene,
tetrakis(4'-carboxy[1,1'-biphenyl]-4-il)ethylene,
3,3',5,5'-tetra(4-carboxyphenyl)biphenyl,
N,N,N',N'-tetrakis(4-carboxyphenyl)-biphenyl-4,4'-diamine,
1,3,6,8-tetra(4-carboxyphenyl)pyrene, and
tetrakis(4-carboxyphenyl)porphyrin.

6. The phosphor film according to claim 2, wherein the bidentate ligand is at least one ligand selected from the group consisting of
triethylenediamine,
4,4'-bipyridyl, 1,4-di(4-pyridyl)benzene,
3,6-di(4-pyridyl)-1,2,4,5-tetrazine,
1,2-di(4-pyridyl)ethane, 1,2-di(4-pyridyl)ethylene, and
1,4-bis[1H-imidazole-1-il)methyl]benzene.

7. The phosphor film according to claim 1, wherein the phosphor film has a thickness of from 100 nm to 500 μm.

8. The phosphor film according to claim 1, wherein the target molecule adsorbed by the phosphor film is desorbed by heating the phosphor film.

9. A molecule detecting device comprising:

a collector configured to collect a fluid comprising a target molecule;

a fluorescence emitter comprising a detector comprising the phosphor film according to claim 1, and a light source configured to emit light that excites the metal organic framework;

a photoelectric converter configured to convert the fluorescence to an electrical signal; and a signal processor configured to process the electrical signal.

10. The phosphor film according to claim 1, wherein the metal organic framework has a pillared layered structure.

11. The phosphor film according to claim 1, wherein the interaction causes a change in an interval of unit lattices of the metal organic framework to change an emission spectrum of the fluorescence.

* * * * *